United States Patent
Chowdhury et al.

(10) Patent No.: US 12,321,687 B2
(45) Date of Patent: Jun. 3, 2025

(54) METHOD AND APPARATUS FOR SEGMENTING A MEDICAL TEXT REPORT INTO SECTIONS

(71) Applicant: Siemens Healthineers AG, Forchheim (DE)

(72) Inventors: Shaika Chowdhury, Chicago, IL (US); Halid Yerebakan, Carmel, IN (US); Yoshihisa Shinagawa, Downingtown, PA (US)

(73) Assignee: Siemens Healthineers AG, Forchheim (DE)

( * ) Notice: Subject to any disclaimer, the term of this patent is extended or adjusted under 35 U.S.C. 154(b) by 619 days.

(21) Appl. No.: 17/713,673

(22) Filed: Apr. 5, 2022

(65) Prior Publication Data

US 2022/0398374 A1    Dec. 15, 2022

(30) Foreign Application Priority Data

Jun. 15, 2021  (EP) ..................... 21179656

(51) Int. Cl.
*G06F 40/30*   (2020.01)
*G06F 40/123*  (2020.01)
*G06F 40/166*  (2020.01)
*G06F 40/279*  (2020.01)
*G06N 3/08*    (2023.01)
*G16H 15/00*   (2018.01)

(52) U.S. Cl.
CPC .......... *G06F 40/166* (2020.01); *G06F 40/123* (2020.01); *G06F 40/279* (2020.01); *G06F 40/30* (2020.01); *G06N 3/08* (2013.01); *G16H 15/00* (2018.01)

(58) Field of Classification Search
None
See application file for complete search history.

(56) References Cited

U.S. PATENT DOCUMENTS

| | | | |
|---|---|---|---|
| 2018/0336183 A1* | 11/2018 | Lee ..................... | G06N 5/022 |
| 2019/0347269 A1* | 11/2019 | Xu ..................... | G06F 40/295 |
| 2020/0117712 A1* | 4/2020 | Xu ..................... | G16H 30/40 |

(Continued)

OTHER PUBLICATIONS

Fiok, Krzysztof et al: "Comparing the Quality and Speed of Sentence Classification with Modern Language Models"; Applied Sciences; vol. 10, No. 10, May 14, 2020 (May 14, 2020), 3386.

(Continued)

*Primary Examiner* — Nafiz E Hoque (57) ABSTRACT

A framework for segmenting a medical text report into sections is disclosed. For each sentence of the report, a first sentence representation is determined by inputting a word-level context representation for each sentence sequentially into a neural network. A second sentence representation is determined by inputting an aggregated representation for each sentence sequentially into another neural network. For each sentence, a third sentence representation is determined based on a combination of the first and second sentence representations, and a section classification for the sentence is determined by inputting the third sentence representation into a section classifier. Each sentence is assigned the section classification determined for the sentence.

20 Claims, 5 Drawing Sheets

(56) References Cited

U.S. PATENT DOCUMENTS

2022/0058342 A1* 2/2022 Fan .......................... G06N 5/04

OTHER PUBLICATIONS

Wieting, John, et al. "Towards universal paraphrastic sentence embeddings." arXiv preprint arXiv:1511.08198 (2015).
Apostolova, E., Channin, D. S., Demner-Fushman, D., Furst, J., Lytinen, S., & Raicu, D. (2009, September). Automatic segmentation of clinical texts. In 2009 annual international conference of the IEEE engineering in medicine and biology society (pp. 5905-5908). IEEE.
Anonymous: "Sentence Embedding Models"; Oct. 26, 2020 (Oct. 26, 2020), XP055866850.
Anonymous: "4 Sentence Embedding Tecniques One Should Known, With Python Codes"; Aug. 25, 2020 (Aug. 25, 2020), XP055866861.
EP Search report in EP Patent Application No. 21179656.0, dated Dec. 9, 2021, 10 pages.

* cited by examiner

Fig. 1

|  | | 220 |
|---|---|---|
| Description { $s_1$ | MRI Orbit/Face/Neck with MR Angiography of the Head – An infant with facial mass. |
| Clinical History { $s_2$ | 1-day-old female with facial mass. |
| Findings { $s_3$ | MRI orbits/face/neck: There is a pedunculated mass measuring 5.7 x 4.4 x 6.7 cm arising from the patient's lip on the right side. |
| $s_4$ | The mass demonstrates a heterogeneous signal. |
| $s_5$ | There is also heterogeneous enhancement which may relate to a high vascular tumor given the small amount of contrast for the exam. |
| $s_6$ | The origin of the mass from the upper lip demonstrates intact soft tissue planes. |
| $s_7$ | Limited evaluation of the head demonstrates normal appearing midline structures. |
| $s_8$ | Incidental note is made of a small arachnoid cyst within the anterior left middle cranial fossa. |
| $s_9$ | The mastoid air cells on the right are opacified; while the left demonstrates appropriate aeration. |

| Section | Sentence |
|---|---|
| Description | $s_1$ |
| Clinical History | $s_2$ |
| Findings | $s_3$; $s_4$; $s_5$; $s_6$; $s_7$; $s_8$; $s_9$ |

METHOD AND APPARATUS FOR SEGMENTING A MEDICAL TEXT REPORT INTO SECTIONS

CROSS-REFERENCE TO RELATED APPLICATION

This application claims the benefit of priority from European Patent Application No. 21179656.0, filed on Jun. 15, 2021, the contents of which are incorporated by reference.

TECHNICAL FIELD

The present disclosure relates to a method and an apparatus for section segmentation, more specifically for segmenting a medical text report into sections.

BACKGROUND

Reports, such as medical text reports, are often in the form of free-text narratives. For example, a significant amount of patient information produced in hospitals is documented as free-text by caregivers in the form of clinical notes or other medical text reports. These texts can contain important insights and observations made by the caregiver about the patient's health. These texts often have different sections, for example information about a patient's past medical conditions can be found in a 'clinical history' section, whereas observations and findings by the caregiver on the patient's current health can be found in a 'findings' section.

Efficient retrieval of stored information contained within the medical text reports presents problems. For example, an entire text report may need to be retrieved even in the case where only information in a particular section of the report is needed, which is inefficient.

Section segmentation (i.e., automatically partitioning a text report into its constituent sections) is an important task as it can facilitate the precise and efficient retrieval of information contained within the text report. This may be useful for caregivers, for example a referring physician in an emergency department may only wish to view the information in a specific section of a radiology report in order to inform an urgent procedure. However, this may also allow for the efficient running of downstream computer-implemented tasks, such as document summarization and comparison, and information extraction.

In order to allow the benefits of section segmentation of improved information retrieval efficiency, it is important that the parts of the text in the report are accurately and reliably assigned to the correct section. It is therefore desirable to improve the accuracy and reliability with which parts of text of a report are assigned to a section.

A known section segmentation method for clinical texts treats the section segmentation as a text classification problem, where each part of the text (i.e., sentence or section) is individually mapped onto a pre-defined class label. This known section segmentation, however, has drawbacks. Firstly, the accuracy and reliability of the mapping of individual sentences to pre-defined class labels in the known section segmentation is sub-optimal. Secondly, the known section segmentation involves the hand-crafting of features on which the classification is based, which is both labor intensive and fails to generalize well on different, unseen, layouts of text reports.

SUMMARY

According to one aspect of the present framework, there is provided a computer implemented method for segmenting a medical text report into sections, the medical text report comprising a plurality of sentences. The method may include: (a) for each sentence, obtaining a word embedding for each of a plurality of words of the sentence; (b) for each sentence, determining a first sentence representation for the sentence. The first sentence representation may be determined by: for each sentence, inputting the word embeddings for each of the plurality of words of the sentence sequentially into a first neural network to generate a word-level context representation for the sentence; and inputting the word-level context representation for each sentence sequentially into a second neural network thereby to generate the first sentence representation for each sentence.

The method may further include: (c) for each sentence, determining a second sentence representation for the sentence by: for each sentence, applying an aggregating operation to the word embeddings for the sentence to generate an aggregated representation for the sentence; and inputting the aggregated representation for each sentence sequentially into a third neural network thereby to generate the second sentence representation for each sentence; (d) for each sentence, determining a third sentence representation based on a combination of the first sentence representation and the second sentence representation for the sentence; (e) for each sentence, determining a section classification for the sentence by inputting the third sentence representation for the sentence into a section classifier; and (f) for each sentence, assigning the sentence the section classification determined for the sentence.

DETAILED DESCRIPTION

Figure 1:
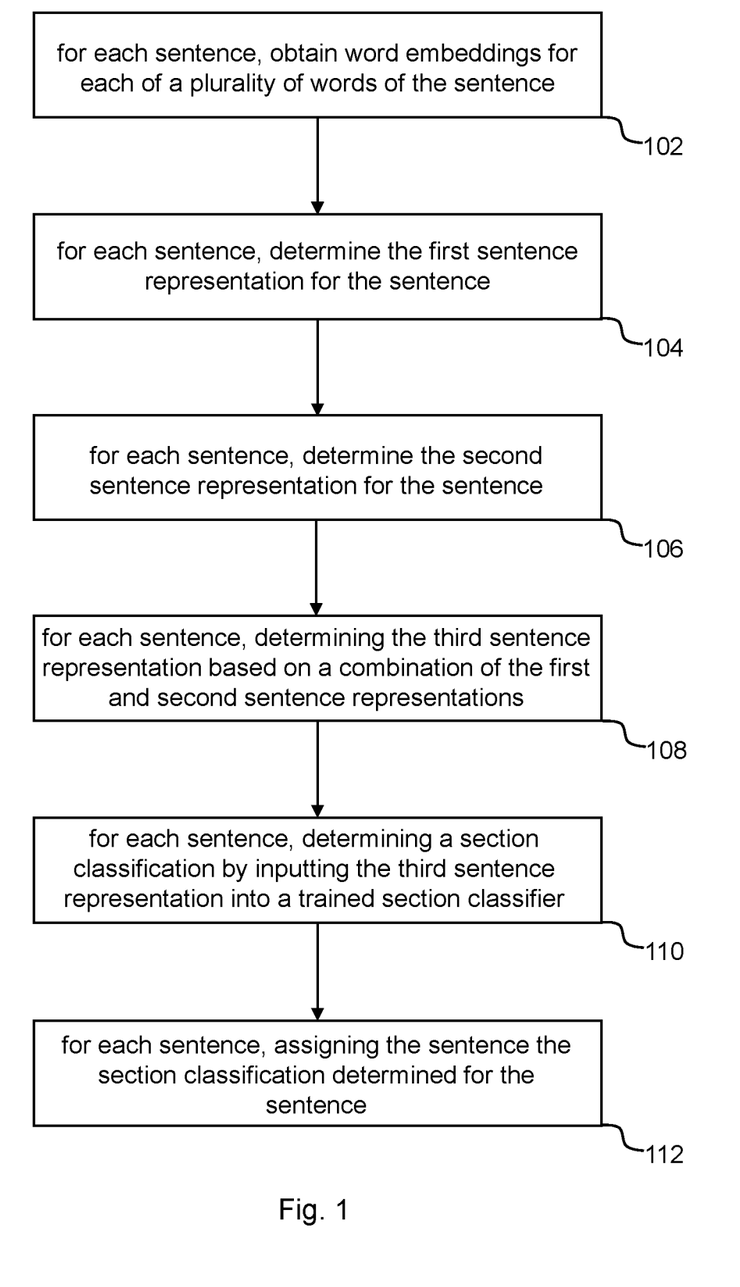
FIG. 1 is flow diagram illustrating schematically a method for segmenting a medical text report into sections, according to an example.
Figure 2:
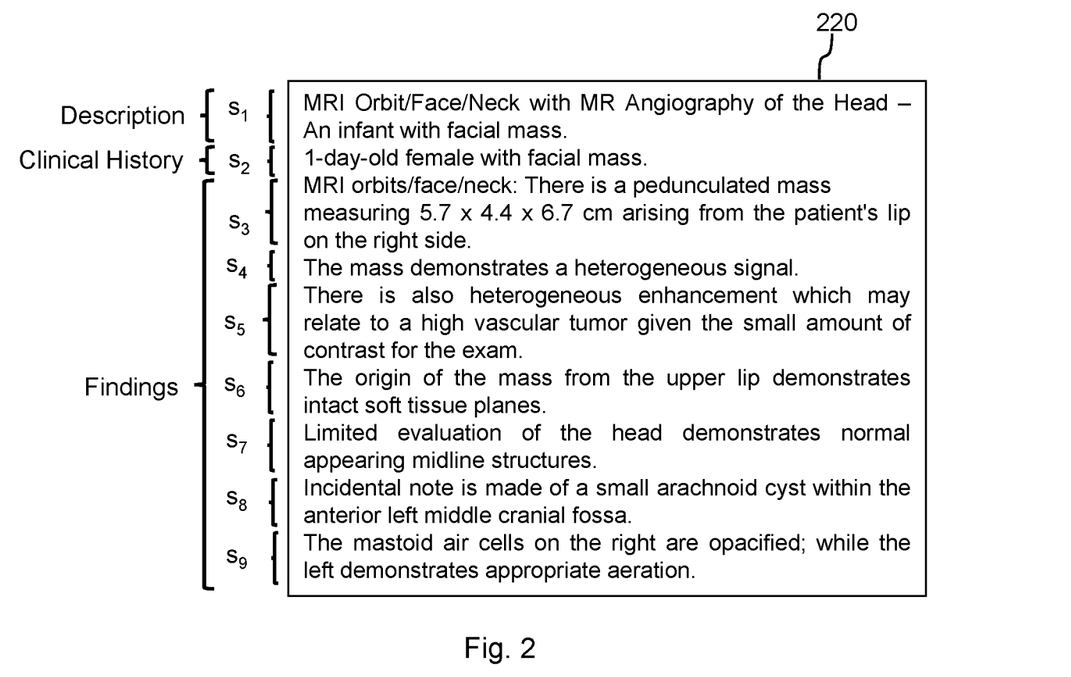
FIG. 2 is a diagram illustrating schematically an example of a medical text report.

Referring to FIG. 1, there is illustrated a computer implemented method for segmenting a medical text report into sections. An example of a medical text report to which the method may be applied is illustrated in FIG. 2. As shown in FIG. 2, the exemplary medical text report 220 includes a plurality of (in this example nine) sentences, $S_1$ to $S_9$. Each sentence comprises a plurality of words. The exemplary medical text report 220 is in the form of a free-text narrative, i.e., it consists of a continuous block of text. In this example, the medical text report is a radiology report, specifically a Magnetic Resonance Imaging (MRI) report. Illustrated in FIG. 2 are notional sections into which the medical text report 220 would ideally be segmented. Specifically, sentence $S_1$ would ideally be part of a 'Description' section (i.e., the section which describes the medical text report), sentence $S_2$ would ideally be in a 'Clinical History' section (i.e., the section which described the clinical history of the patient), and sentences $S_3$ to $S_9$ would ideally be in a 'Findings' section (i.e. the section which describes the clinical findings of the radiographer on assessment of the MRI image). As an illustrative example, a task of the method and apparatus disclosed herein may be to automatically segment the medical text report 220 into these sections, i.e., to assign each sentence $S_1$ to $S_9$ a classification k corresponding to the section in which the sentence would ideally be included.

Returning to FIG. 1, in broad overview, the computer implemented method comprises:

(a) in step 102, for each sentence $s_i$, obtaining a word embedding $w_{it}$ for each of a plurality of words of the sentence;

(b) in step 104, for each sentence $s_i$, determining a first sentence representation $c_{senti}$ for the sentence by:
  (i) for each sentence, inputting the word embeddings $w_{it}$ for each of the plurality of words of the sentence sequentially into a first trained neural network to generate a word-level context representation $c_{wordi}$ for the sentence; and
  (ii) inputting the word-level context representation $c_{wordi}$ for each sentence sequentially into a second trained neural network thereby to generate the first sentence representation $c_{senti}$ for each sentence;

(c) in step 106, for each sentence $s_i$, determining a second sentence representation $g_i$ for the sentence by:
  (i) for each sentence, applying an aggregating operation to the word embeddings for each of the plurality of words of the sentence to generate an aggregated representation $p_i$ for the sentence; and
  (ii) inputting the aggregated representation $p_i$ for each sentence sequentially into a third trained neural network thereby to generate the second sentence representation $g_i$ for each sentence;

(d) in step 108, for each sentence $s_i$, determining a third sentence representation $u_i$ based on a combination of the first sentence representation $c_{senti}$ and the second sentence representation $g_i$ for the sentence;

(e) in step 110, for each sentence $s_i$, determining a section classification $k_i$ for the sentence by inputting the third sentence representation $u_i$ for the sentence into a trained section classifier; and (f) in step 112, for each sentence $S_1$ to $S_9$, assigning the sentence the section classification $k_i$ determined for the sentence.

By this method, each sentence $s_i$ may be accurately and reliably assigned a section classification (e.g., 'Description', 'Clinical History', or 'Findings') and hence accurate and reliable section segmentation of medical text reports may be provided for.

Specifically, the text within a medical text report is sequential in nature. As such, the section to which a sentence would ideally be assigned may be influenced by the sequential context of the sentence (i.e., the sentences that precede and/or are subsequent to the sentence). In order to implement this, according to features (b) and (c), representations for each sentence (based on word embeddings) are passed sequentially into trained neural networks, which may be for example Recurrent Neural Networks, RNNs, to generate sentence representations (i.e., feature vectors) that encode the sequential context of each sentence.

However, the inventors have identified that a particularly accurate/reliable section classification can be obtained by encoding sequential context of sentences by combining two different but complementary branches or approaches to generating sentence representations: As per feature (b), a first, 'local', branch takes a hierarchical approach by first determining a word-level context representation for the sentence (by passing word embeddings sequentially into a first neural network, e.g. a first RNN) and then determining a first sentence representation for the sentence encoding the sentence-level sequential context (by passing the word-level context representations sequentially through a second trained neural network, e.g. a second RNN). This helps capture the fine-grained nuances between local sentences, such as between sentences within a section. On the other hand, as per feature (c), a second, 'global', branch takes an aggregated representation for the sentence (e.g., an average of the word embeddings for the sentence) and uses this to determine a second sentence representation encoding sentence-level sequential context (by passing the aggregated representations sequentially through a trained third neural network, e.g., a third RNN). This helps capture more course grained context changes between sentences, such as between sentences in different sections.

Combining the sentence representations from both branches (e.g., by concatenating them) as per feature (d) and inputting this combination into a trained section classifier to determine a section classification for each sentence as per feature (e) leads to more accurate and/or reliable assignment of section classifications to each sentence as per feature (f), for example as compared to using either branch alone. Accordingly, accurate and/or reliable section segmentation is provided for.

In some examples, the method may comprise generating output data in which the text of the medical text report 220 is segmented into sections, each section being associated with a particular section classification $k_i$ and including those sentences of the medical text report 220 to which the particular section classification $k_i$ has been assigned.

Figure 3:
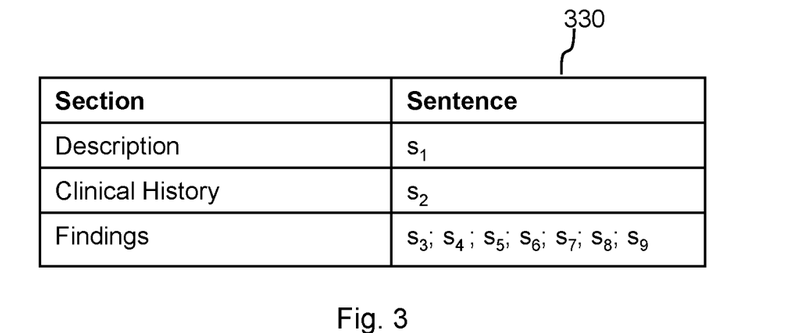
FIG. 3 is a diagram illustrating schematically a data structure according to an example.

An example of generated output data is illustrated in FIG. 3. Referring to FIG. 3, the output data takes the form of a table 330 comprising a 'Section' column listing the section classifications 'Description', 'Clinical History' and 'Findings'; and a 'Sentence' column listing, for each particular section classification, the sentences $S_1$ to $S_9$ that have been assigned the particular section classification. In FIG. 2, the sentences are represented by their reference signs $S_1$ to $S_9$ for brevity. In some examples, the output data 330 may comprise such tokens representing the sentences rather than the actual text itself. For example, the tokens may act as pointers to the text itself, which may be stored separately. In other examples, the output data 330 may include the text of each sentence (e.g., as per FIG. 3 but in which the reference signs $S_1$ to $S_9$ are replaced by the text of the corresponding sentence of the medical text report 220).

In some examples, the method may comprise storing the output data 330 in a structured storage such that each section is stored in association with a respective associated section classification. For example, the data of the table 330 of FIG. 3 may be stored in a database, such as a relational database. For example, the relational database may relate each section classification to the associated section of the medical text report 220 (i.e., the sentences to which the section classification has been assigned, for example in the format illustrated in FIG. 3).

Storing the output data in this way may provide for the efficient retrieval of information contained within the medical text reports. For example, where only a particular section of the report is needed, the particular section can be efficiently and precisely queried and extracted from the database, for example as compared to extracting the entire medical text report. For example, the structured storage may be accessed and interrogated by online medical query platforms and/or other information retrieval systems to return information to a user that is more relevant and/or precise with respect to a search query. The efficient extraction of information may, in turn, allow for the efficient running of downstream computer-implemented tasks, such as document summarization and comparison, and information extraction.

Figure 4:
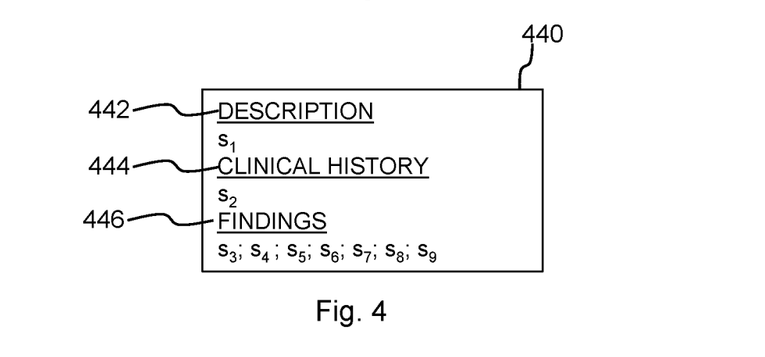
FIG. 4 is a diagram illustrating schematically an output data according to an example.

Another example of output data that may be generated is illustrated in FIG. 4. In this example, the output data 440 is in the form of a medical text report, similar to that of FIG. 2, but in which section separators 442, 444, 446 have been inserted into the text according to the section classification assigned to each sentence. In the illustrated example, the section separators are section identifiers 442, 444, 446, and more specifically are headings ('DESCRIPTION', 'CLINICAL HISTORY', and 'FINDINGS') corresponding to the section classifications and each being placed at the start of the section (i.e., group of one or more sentences) to which the corresponding section classification has been assigned. In other examples (not shown), the section separators may take other forms, such as a line or other mark between sections to indicate the delineation between one section and an adjoining section. Again, in FIG. 4, for brevity, the references $S_1$ to $S_9$ are used in place of the actual text of the sentences but it will be appreciated that in some examples the output data 440 may include the actual text of the sentences to which the references $S_1$ to $S_9$ refer. The output data 440 may allow for a medical text report to be provided in which the different sections are readily discernible, for example as compared to the medical text report 220 in FIG. 2 in which the different sections are not readily discernable.

In some examples, the method may comprise displaying the output data 330, 440 on a display, such as a computer monitor (not shown). This may allow a user to readily discern the different sections of the medical text report, and hence may allow for a more efficient interaction of the user with the information contained in the report.

Example details of the steps of the method described above with reference to FIGS. 1 to 4 will now be described with additional reference to FIG. 5.

Figure 5:
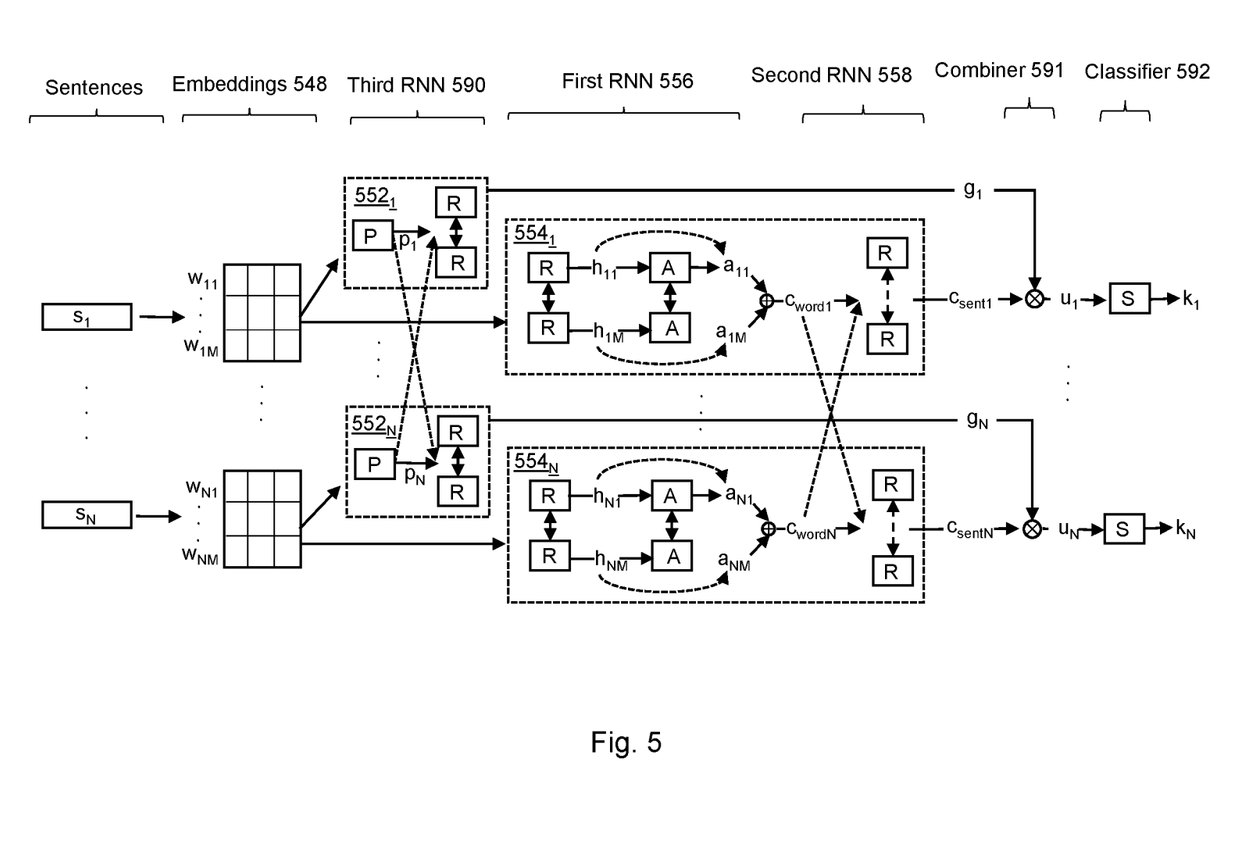
FIG. 5 is a diagram illustrating schematically functional blocks of a neural network according to an example.

FIG. 5 is a schematic diagram illustrating an example process flow through functional blocks of a neural network by which the method may be implemented. The example neural network architecture comprises a first module or branch 554 comprising the first RNN 556 and the second RNN 558, a second module or branch 552 comprising the third RNN 590, a combiner 591 and the classifier 592.

As is known, the input to a RNN is sequential and the state or output of the RNN resulting from a certain input is dependent on or influenced by the state or output resulting from a previous input. In FIG. 5, in order to represent the sequential nature of the input to the various RNNs, two states of the neural network are illustrated, one for sentence $s_1$ (the first sentence in the medical text report) and one for sentence $s_N$ (the last sentence in the medical text report). The three dots between the states are to illustrate that the same process also occurs for the sentences between the first and last sentences. The dotted arrows between the second RNN 558 in the two states is to illustrate that the first sentence representations $c_{wordi}$ for each sentence $s_i$ are being input sequentially into the second RNN 588. Similarly, the dotted arrows between the third RNN 590 in the two states is to illustrate that the aggregated representations $p_i$ for each sentence $s_i$ are being input sequentially into the third RNN 590. It will be appreciated that this is an example for illustrative purposes, and that other architectures and process flows may be used in accordance with the method.

As mentioned, the method comprises, in step 102, for each sentence $S_i$, obtaining a word embedding $w_{it}$ for each of a plurality of words of the sentence. As illustrated in FIG. 5, N is the total number of sentences $s_i$ in the medical text report to be segmented, and M is the total number of words t of a given sentence $s_i$. The sentences may be segmented and extracted from the medical text report, for example by a pretrained neural sentence tokenizer. The embeddings 548 for each of a plurality of words of the sentence are then obtained. In this example, for each sentence $S_i$, a word embedding $w_{it}$ is obtained for each word of the sentence.

As is known, a word embedding is a vector representing the meaning or semantics of a word in a multidimensional space. Libraries of pre-trained word embeddings exist. In some examples, the word embedding for a given word may be obtained by looking-up the word embedding for the given word in such a library. In some examples, word embeddings may be obtained using a pre-trained model. For example, each word of the medical text report may be passed through a WordPiece tokenizer to return a set of tokens, each token representing a word, and the set of tokens may be passed through a pre-trained model to generate the word embedding for each word. For example, a BERT (Bideirectional Encoder Representations from Transformers) model may be used, whereby each sentence is passed through a BERT WordPiece tokenizer, and each resulting token passed through a pre-trained BERT model to obtain therefrom the embedding $w_{it}$ for each word. This may allow to accurately capture the similarities and regularities between words. It will be appreciated that in some examples, the word embeddings may be obtained in other ways.

As mentioned, the method comprises, in step 104, for each sentence, determining a first sentence representation $c_{senti}$ for the sentence.

Specifically, as a first part of step 104, for each sentence $S_i$, the word embeddings $w_{it}$ for each of the plurality of words of the sentence are input sequentially into the trained first RNN 556 (recurrent neural network) to generate a word-level context representation $c_{wordi}$ for the sentence.

In some examples, the first RNN 556 may be a bi-directional recurrent neural network. That is, the first RNN may incorporate, for each word, both past and future context into the hidden state $h_{it}$ calculated for the word (i.e., context of the words preceding the word as well as context of the words subsequent to the word in the sentence). This may allow for both the preceding and subsequent context of each word to be incorporated into the word-level context representation $c_{wordi}$ for the sentence, which may in turn improve the accuracy with which the word-level context of the sentences can be represented.

In some examples, the first RNN 556 may comprise one or more Gated Recurrent Units (GRUs) R. This may allow for the hidden states $h_{it}$ for each word to be calculated with high performance and computational efficiency, for example as compared to a vanilla RNN or a Long Short-Term Memory (LSTM) unit. In the case that the first RNN 566 is a bidirectional RNN, the first RNN may comprise at least two GRUs R, one operating in a different sequential direction to the other.

For example, for each sentence $s_i$, for the word having word embedding $w_{it}$, the hidden state $h_{it}$ in a GRU R may be computed with an update gate and a reset gate using the following equations:

$$z_{it} = \sigma(W_z w_{it} + V_z h_{it-1} + b_z) \quad (1)$$

$$r_{it} = \sigma(W_r w_{it} + V_r h_{it-1} + b_r) \quad (2)$$

$$\hat{h}_{it} = \tanh(W_h w_{it} + V_h (r_{it} \odot h_{it-1}) + b_h) \quad (3)$$

$$h_{it} = (1 - z_{it}) \odot \hat{h}_{it} + z_{it} \odot h_{it-1} \quad (4)$$

where $\odot$ denotes the element-wise product of two vectors, $\sigma$ is a sigmoid function, W and V are parameter matrices, b is a parameter vector, $h_{it}$ is the hidden state i.e., the output vector, $\hat{h}_{it}$ is the candidate activation vector, $z_{it}$ is the update gate vector, and r is the reset gate vector. In the case of the bidirectional GRUs (BiGRU), one GRU calculates a forward hidden state and another calculates the backward hidden state, and these may be concatenated to represent the hidden state $h_{it}$ of the word. Accordingly, the BiGRU may encode the word sequence for each sentence $s_i = \{w_t, 1:M\}$ into the hidden state sequence $h_i = \{h_t, 1:M\}$.

In some examples, for each sentence, the hidden states $h_{it}$ output from the first RNN 556 for each word of the sentence $s_i$ may be summed to obtain the word-level sentence representation $c_{wordi}$ for the sentence.

However, in some examples, as illustrated in FIG. 5, generating the word-level context representation $c_{wordi}$ for each sentence may involve employing an attention mechanism A. Employing an attention mechanism may allow the word-level context representation $c_{wordi}$ to an be biased towards the most semantically-informative words relevant to the sentence context. This may, in turn, help improve the section classification accuracy.

For example, applying the attention mechanism may comprise, for each word of the sentence: determining a score $a_{it}$ indicating a relevance of the word $w_{it}$ to a context $z_i$ of the sentence $s_i$; and weighting a contribution $h_{it}$ associated with the word $w_{it}$ to the word-level context representation $c_{wordi}$ using the score $a_{it}$ determined for the word. For example, the contribution $h_{it}$ associated with the word $w_{it}$ to the word-level context representation $c_{wordi}$ may comprise the hidden state $h_{it}$, associated with the word, of a recurrent unit R of the first RNN 556. The word-level context representation $c_{wordi}$ for the sentence may comprise a weighted sum of the hidden states ha associated with the words of the sentence $s_i$, each hidden state $h_{it}$ being weighted by the score $a_{it}$ determined for the associated word. The context of the sentence $z_i$ may be represented by an aggregation of the hidden states $h_{it}$ of all of the words of the sentence. For example, the aggregation of the hidden states may be a concatenation of the hidden states $h_{it}$ for all of the words of the sentence.

The score $a_{it}$ indicating the relevance of the word to the context $z_i$ of the sentence may be determined based on the output of an activation function (e.g., tan h) applied between the hidden state $h_{it}$ associated with the word and the aggregation $z_i$ of the hidden states. For example, the score $a_{it}$ between each hidden state $h_{it}$ and the context vector $z_i$ for the sentence $s_i$ may be computed using the following equations:

$$\text{score}(z_i, h_{it}) = v_a^T \tanh(W_1 z_i + W_2 h_{it}) \quad (5)$$

$$a_{it} = \frac{\exp(\text{score}(z_i, h_{it}))}{\sum_{t=1}^{M} \exp(\text{score}(z_i, h_{it}))} \quad (6)$$

where $v_a$, $W_1$, and $W_2$ are learned weight matrices. As mentioned, the context vector $z_i$ for the sentence $s_i$ may be the concatenation of the hidden states $h_{it}$ of all of the words of the sentence. A higher value of the relevance score $a_{it}$ indicates a higher salience of the information carried by the word with respect to the overall sentence context $z_i$.

The hidden states $h_{it}$ for a sentence may then be transformed into a word-level context representation $c_{wordi}$ for the sentence $s_i$ by weighing each hidden state $h_{it}$ with its score $a_{it}$, for example using the following equation:

$$c_{wordi} = \sum_{t=1}^{M} a_{it} h_{it} \quad (7)$$

This may be repeated for each sentence to obtain the word-level content representation $c_{wordi}$ for each sentence.

In the second part of step 104, the word-level context representation $c_{wordi}$ for each sentence is input sequentially into the second trained RNN 558 thereby to generate the first sentence representation $c_{senti}$ for each sentence $s_i$.

In some examples, the second RNN 558 may be a bi-directional RNN. In some examples, the second RNN 558 may comprise one or more Gated Recurrent Units R. For example, the second RNN 558 may operate similarly to as described above for the first RNN 556, but for example with the word-level context representation $c_{wordi}$ for each sentence being sequentially input into the second RNN 558 instead of the word embedding $w_{it}$ for each word of a sentence as per the first RNN 556. For example, the second RNN 558 may operate using equations (1)-(4) listed above, except with the word embedding $w_{it}$ for each word of a sentence being replaced with the word-level context representation $c_{wordi}$ for each sentence.

The second part of step 104 captures into the first sentence representation $c_{senti}$ for each sentence the semantically relevant context from the surrounding sentences. The first sentence representation $c_{senti}$ for each sentence, having been based on the word-level context representation $c_{wordi}$ for each sentence, encodes the fine-grained topical semantics of the sentence among the other sentences, and can help indicate more nuanced and fine-grained relationships between sentences, such as between sentences within a section.

As mentioned, the method comprises, in step 106, for each sentence $s_i$, determining a second sentence representation $g_i$ for the sentence.

A first part of the step 106 comprises, for each sentence $s_i$, applying an aggregating operation P to the word embeddings $w_{it}$ for the sentence to generate an aggregated representation $p_i$ for the sentence. For example, applying the aggregating operation P may comprise taking the mean of the word embeddings of the words of the sentence. In this case the aggregated representation $p_i$ for the sentence may be the average (mean) of the word embeddings $w_{it}$ of the words of the sentence. The mean operation may be particularly effective in that it is computationally simple but allows for all of the words of the sentence to contribute to the aggregated representation $p_i$, thereby effectively capturing the overall or global context of the sentence. In some examples, the mean may be calculated by applying a mean pooling operation. It will be appreciated that in some examples, other aggregating operations may be used. For example, in some examples, the aggregating operation may be a pooling operation, applied to the word embeddings $w_{it}$ for the sentence, to generate a pooled representation $p_i$ for the sentence. For example, the pooling operation may be max-pooling (e.g., where the maximum value of the word embedding $w_{it}$, or of sub regions of the word embedding $w_{it}$, are taken as representative values of the word embedding), or for example min-pooling (e.g., where the minimum value of the word embedding $w_{it}$, or of sub regions of the word embedding $w_{it}$, are taken as representative values of the word embedding).

A second part of step 106 comprises inputting the aggregated representation $p_i$ for each sentence sequentially into the third trained RNN 590 thereby to generate the second sentence representation $g_i$ for each sentence. For example, the third RNN 590 may be a bidirectional RNN, i.e., whereby the context of both preceding sentences and subsequent sentences are encoded into the second sentence representation $g_i$ for the sentence. In some examples, similarly to as described above, the third RNN may comprise GRUs R. The second sentence representation $g_i$ for each sentence, having been based on the aggregated or global representation $p_i$ for each sentence, encodes the coarse-grained topical semantics of the sentence among the other sentences, and can help indicate more course grained context changes between sentences, such as between sentences in different sections.

As mentioned, in step 108, the method comprises, for each sentence, determining a third sentence representation $u_i$ based on a combination of the first sentence representation $c_{senti}$ and the second sentence representation $g_i$ for the sentence. For example, this may be performed by the combiner 591 module of the neural network of FIG. 5. For example, the third or unified sentence representation $u_i$ for a given sentence may be determined based on a concatenation of the first sentence representation $c_{senti}$ and the second sentence representation $g_i$ for the given sentence, for example by concatenating the first sentence representation $c_{senti}$ and the second sentence representation $g_i$ for the given sentence. More formally, the third sentence representation may be written as $u_i=[c_{senti}; g_i]$.

As mentioned, the method comprises, in step 108, for each sentence, determining a section classification $k_i$ for the sentence by inputting the third sentence representation $u_i$ for the sentence into a trained section classifier. For example, the classifier 592 may be trained to determine the section classification for a sentence based on an input third sentence representation for the sentence. For example, the classifier may comprise a fully connected softmax layer S. This may give the probabilities for each of a plurality of pre-defined section classifications that the input sentence $s_i$ belongs to the section classification. For example, the softmax layer may output the probability that a given sentence belongs to the section 'Description', 'Clinical History' or 'Findings', although it will be appreciated that the trained section classifier may be configured to output probabilities for any number of pre-defined section classifications, in dependence on the section classifications on which it has been trained. In some examples, the section classifier may determine, as the section classification for an input sentence, the section classification associated with the highest probability output by the softmax layer.

As mentioned, the method comprises, in step 110, for each sentence, assigning the sentence the section classification determined for the sentence. For example, if the section classification $k_1$ for the sentence $s_1$ is determined as 'Description', this section classifier is assigned to the sentence. For example, a tag may be assigned to data representing the sentence to indicate the associated classification. In some examples, output data may be generated and stored, for example as described above with reference to FIGS. 2 to 3.

The section classification for each sentence being based on the combination $u_i$ of the both the more fine-grained first sentence representation $c_{senti}$ and the more course-grained second sentence representation $g_i$ allows for more accurate and/or reliable assignment of the section classification, for example as compared to using either one of the sentence representations alone. Accordingly, accurate and/or reliable section segmentation may be provided for. It is noted that an example demonstration of this is described below with reference to FIG. 7.

Figure 6:
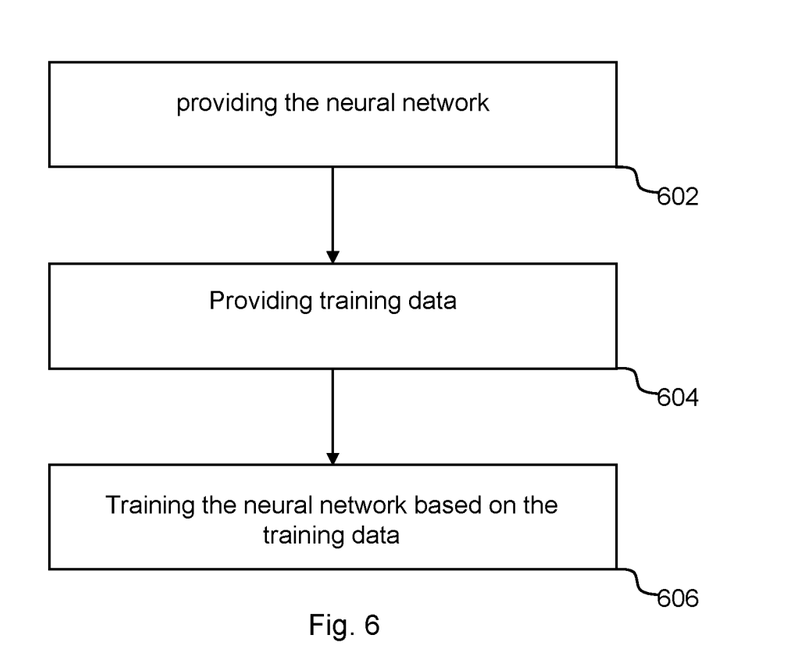
FIG. 6 is a flow diagram illustrating schematically a method of training a neural network for segmenting a medical text report into sections, according to an example.

Referring to FIG. 6, there is illustrated a computer implemented method of training a neural network for segmenting a medical text report into sections. For example, the first neural network, the second neural network, the third neural network and the classifier described above with reference to FIGS. 1 to 4 may be trained according to the method outlined in FIG. 6. For example, the method described with reference to FIG. 6 may be used to train the example neural network described above with reference to FIG. 5. The method comprises, in step 602, providing the neural network. For example, the neural network may be as described above with reference to FIG. 5.

The neural network comprises a first sentence representation module 554 comprising: (i) a first neural network 556 configured to generate, for each sentence $s_i$, a word-level context representation $c_{wordi}$ for the sentence based on sequential input of word embeddings $w_{it}$ for each of a plurality of words of the sentence. For example, the first neural network 556 may be an RNN, and in some examples may be the same as or similar to the first RNN 556 described above with reference to FIG. 5. The first sentence representation module 554 also comprises: (ii) a second neural network 558 configured to generate, for each sentence, a first sentence representation $c_{senti}$ for the sentence based on sequential input of the word-level context representation $c_{wordi}$ for the sentence. For example, the second neural network 558 may be an RNN, and in some examples may be the same as or similar to the second RNN 558 described above with reference to FIG. 5.

The neural network comprises a second sentence representation module 552 comprising: a third neural 590 configured to generate, for each sentence, a second sentence representation $g_i$ based on sequential input of an aggregated representation $p_i$ for the sentence, the aggregated representation having been generated by applying an aggregating operation P to the word embeddings $w_{it}$ of each of the plurality of words of the sentence. For example, the third neural network 590 may be an RNN, and ins some examples may be the same as or similar to the third RNN 590 described above with reference to FIG. 5.

The neural network comprises a section classifier 592 configured to, for each sentence, determine a section classification $k_i$ for the sentence based on input of a third sentence representation $u_i$ for the sentence, the third sentence representation $u_i$ being a combination of the generated first sentence representation $c_{senti}$ and the generated second sentence representation $g_i$ for the sentence. For example, the section classifier 592 may be the same as or similar to that described above with reference to FIG. 5.

The method comprises, in step 604, providing training data. The training data comprises a plurality of medical text reports, each medical text report comprising a plurality of sentences $s_i$, each sentence comprising a plurality of words, the training data further comprising a ground truth section classification $y_i$ for each sentence indicating the particular section of the medical text report to which the sentence belongs. For example, the sentences of the medical text reports of the training data may have been annotated, for example by an expert or automatically, to indicate the section classification to which the sentence belongs or should belong.

The method comprises, in step 606, training the neural network based on the training data. The neural network is trained to minimize a loss function between the section classifications $k_i$ determined for the sentences by the section classifier 592 and the corresponding ground truth section classifications $y_i$ for the sentences. For example, the loss function may comprise the cross entropy between the section classifications $k_i$ determined for the sentences by the section classifier 592 and the corresponding ground truth section classifications $y_i$ for the sentences. For example, the loss function L may be calculated according to the following equation:

$$L = \Sigma_{F=1}^{R} \Sigma_{i=1}^{N} y_i^r \log(k_i^r) \quad (8)$$

where R is the total number of medical text reports in the training data set, and N is the total number of sentences in each text report r of the training data set.

Training the first RNN 556, second RNN 558, third RNN 590 and classifier 592 in this way allows for both the feature construction (i.e., the generation of the sentence representations) and the model training to be undertaken together automatically without human interaction. This allows the features to be learned through guidance from the model optimization. This reduces the need, as in a known section segmentation, to hand-craft features, and hence reduces the manual labor associated with training the model, as well as providing for better generalization on unseen layouts.

In the example described above with reference to FIG. 5, each of the first neural network, the second neural network, and the third neural network is a Recurrent Neural Network, RNN, and more specifically a bidirectional RNN. However, it will be appreciated that this need not necessarily be the case and that in some examples, other types of neural networks may be used for the first, second and/or third neural networks. For example, in some examples (not shown) other sequential neural networks configured to take a sequential input and produce an output representing sequential context, for example Transformer Neural Networks and the like, may be used.

A demonstration of the effectiveness of the method according to examples disclosed herein in correctly assigning section classifications to sentences in medical text reports is provided. The demonstration is provided for illustrative purposes. Specifically, a study was performed to assess the effectiveness of the method as compared to other models. For the purposes of this illustrative study, parameters for the training of the neural network disclosed herein were as follows: a learning rate of 0.001 for 100 epochs, batch size set to 28, the dimension of the GRU hidden states is set to 100, the dimension of the attention mechanism is set to 10, the BERT word embedding dimension is 768, and all other weights are initialized using a Glorot uniform initializer.

This study was performed for four different data-sets: MtSamples (MT) which consists of transcribed medical reports downloaded from mtsamples.com, NationalRad (NR) which consists of transcribed radiology reports downloaded from nationalrad.com/radiology/reports, JH consisting of sample reports provided from a hospital, and NLP consisting of sample reports provided by another hospital. The data sizes of these data sets are outline below in Table 1, both in terms of number of reports and number of sentences. The dataset ALL includes all of the MT, NR, JH and NLP datasets added together.

TABLE 1

|            | MT   | NR   | JH   | NLP  | ALL   |
|------------|------|------|------|------|-------|
| #Reports   | 267  | 51   | 124  | 81   | 523   |
| #Sentences | 6745 | 1579 | 3894 | 1165 | 13383 |

For the purposes of the illustrative study, each data set was split into 80% training, 10% validation, and 10% testing.

The performance of each model is indicated by a weighted average accuracy, precision, recall, and F-score of whether the section classification of each sentence in the report is predicted correctly (as determined by the ground truth).

The other models to which the performance of the presently disclosed method was compared included a Naïve Bayes (NB) model, a Support Vector Machine (SVM) model, a Maximum Entropy (ME) model, a Random Forest (RF) model, a convolutional neural network (CNN) model, a Multi-Layer Perceptron (MLP) model, a Cross-Segment Bidirectional Encoder Representations from Transformers (CS-BERT) model, a Bi-directional Long Short Term Memory (Bi-LSTM) model, and a Stacked GRU (St-GRU) model. The performance of the NB, SVM, ME, and RF models as compared to the presently disclosed method (MedTextSeg) for the ALL dataset is shown below in Table 2.

TABLE 2

|           | NB    | SVM   | ME    | RF    | MedTextSeg |
|-----------|-------|-------|-------|-------|------------|
| Accuracy  | 65.75 | 70.44 | 36.57 | 71.12 | 90.24      |
| Precision | 67.72 | 71.11 | 13.37 | 71.67 | 94.79      |
| Recall    | 65.75 | 70.45 | 36.57 | 71.11 | 90.24      |
| F-score   | 63.77 | 69.48 | 19.58 | 70.56 | 90.81      |

The performance of the CNN, MLP, CS-BERT, Bi-BERT, and the ST-GRU models as compared to the presently disclosed model (MedTextSeg) for the MT, NR, JH, NLP, and ALL datasets is shown below in Table 3.

TABLE 3

|     |           | CNN   | NLP   | CS-BERT | Bi-BERT | St-GRU | MedTextSeg |
|-----|-----------|-------|-------|---------|---------|--------|------------|
| MT  | Accuracy  | 68.67 | 72.80 | 75.56   | 87.73   | 78.37  | 90.79      |
|     | Precision | 78.93 | 84.96 | 76.08   | 89.90   | 86.79  | 95.87      |
|     | Recall    | 68.67 | 72.80 | 75.56   | 87.73   | 78.37  | 90.79      |
|     | F-Score   | 70.82 | 75.52 | 74.89   | 87.21   | 80.05  | 91.72      |
| NR  | Accuracy  | 72.16 | 73.47 | 90.62   | 93.19   | 77.99  | 97.64      |
|     | Precision | 72.19 | 74.63 | 89.06   | 96.06   | 75.63  | 96.67      |
|     | Recall    | 72.16 | 73.47 | 90.62   | 93.19   | 77.97  | 97.64      |
|     | F-Score   | 71.24 | 73.55 | 889.33  | 93.84   | 76.36  | 97.08      |
| JH  | Accuracy  | 56.72 | 73.22 | 79.48   | 84.92   | 82.11  | 88.66      |
|     | Precision | 59.09 | 77.37 | 85.79   | 83.82   | 88.47  | 91.54      |
|     | Recall    | 56.72 | 73.22 | 79.49   | 84.92   | 82.77  | 88.66      |
|     | F-Score   | 61.24 | 74.44 | 79.81   | 83.47   | 84.07  | 88.92      |
| NLP | Accuracy  | 70.98 | 74.14 | 77.33   | 79.46   | 78.30  | 83.30      |
|     | Precision | 81.74 | 91.99 | 80.41   | 92.21   | 87.04  | 94.38      |
|     | Recall    | 70.98 | 83.87 | 74.14   | 79.46   | 78.30  | 83.30      |
|     | F-Score   | 72.77 | 81.21 | 78.71   | 78.57   | 80.01  | 84.91      |
| ALL | Accuracy  | 73.74 | 77.35 | 82.84   | 85.19   | 80.00  | 90.24      |
|     | Precision | 82.77 | 83.69 | 83.76   | 86.18   | 88.66  | 94.79      |
|     | Recall    | 73.74 | 77.34 | 82.84   | 85.19   | 80.00  | 90.24      |
|     | F-Score   | 75.54 | 78.33 | 82.44   | 84.41   | 81.76  | 90.81      |

As can be seen, the presently disclosed method MedTextSeg is able to outperform all of the comparative models for all of the data sets for each of the Accuracy, Precision, Recall and F-Score metrics. For example, there are percentage improvements of 5.93% accuracy, 9.99% precision, 5.93% recall and 7.58% F-score of the MedTextSeg method/model over Bi-BERT on the ALL dataset. Although CS-BERT, Bi-BERT and St-GRU are sequential models, they only model the local context of each sentence. To the contrary, as discussed above, the presently disclosed method/model is able to also capture the overall topical information within a section by using the second, 'global' encoding module or branch 590 and accordingly can perform better.

An ablation study was also undertaken to illustrate the effect of removing either the first module 554 (comprising the first RNN 556 and the second RNN 558) or the second module 552 (comprising the third RNN 590) on performance. The results are shown below in Table 4 for the ALL dataset, where MedTextSeg indicates the results where the disclosed method/model is used, HEM indicates the results where only the first module 554 is used, and GEM indicates the results where only the second module 552 is used.

TABLE 4

|  | MedTextSeg | HEM | GEM |
|---|---|---|---|
| Accuracy | 90.24 | 83.07 | 89.72 |
| Precision | 94.79 | 90.66 | 92.45 |
| Recall | 90.24 | 83.01 | 89.72 |
| F-Score | 90.81 | 84.27 | 89.48 |

As can be seen, removing either module damages the segmentation performance in comparison to that of the complete model. In particular, the F-score drops by 7.76% with HEM and 1.49% with GEM. This serves to illustrated that using the third sentence representation $u_i$ including both the first sentence representation $c_{senti}$ encoding a more local context and the second sentence representation $g_i$ encoding a more global context of the sentence, as per the method disclosed herein, allows for improved performance, and hence more accurate and/or reliable section segmentation.

Figure 7:
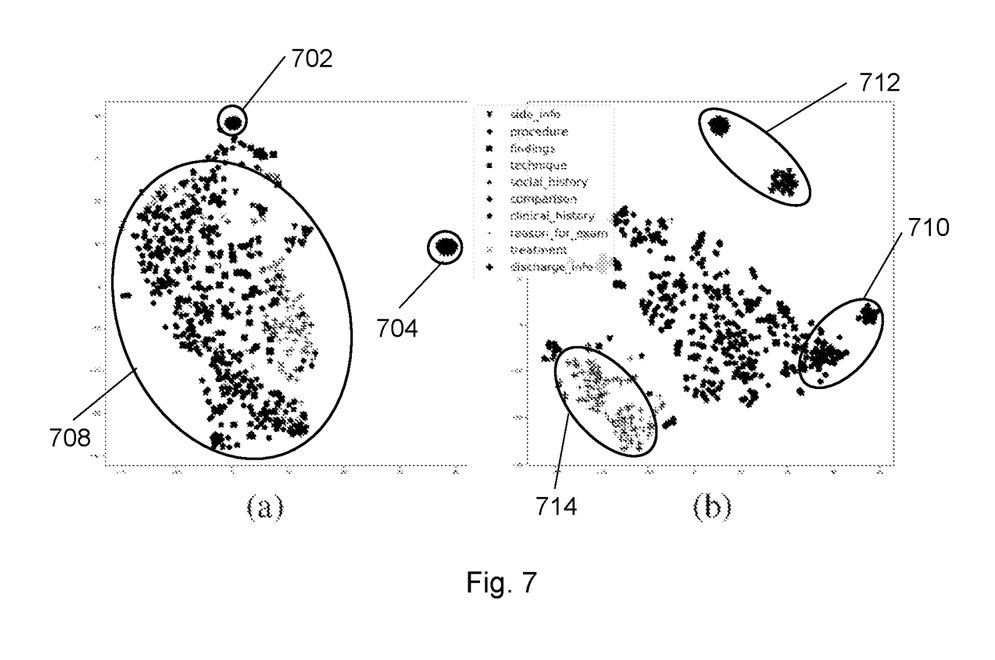
FIGS. 7a and 7b are graphs plotting two-dimensional projections of determined sentence representations for sentences (FIG. 7b) and a comparative model (FIG. 7a)

A qualitative evaluation of the learned features was also performed. For this illustrative study, the output sentence representations from the last layer (i.e., the layer before the softmax layer) in respective models was obtained. In the case of the MedTextSeg model of the present disclosure, this corresponds to the third sentence representation $u_i$ output from the combiner 591. This was compared to the output sentence representations from the MLP model. Specifically, for each sentence of the test set of the training data set, the output sentence representation was projected to a two-dimensional space using Principal Component Analysis (PCA), and then t-Distributed Stochastic Neighbor Embedding (T-SNE) was applied to group the sentences based on the section that they belong to according to the ground truth classifications. The results are shown in FIG. 7. The axes in both the graph of FIG. 7(a) and the graph of FIG. 7(b) are the two dimensions of feature space onto which the output sentence representations were projected using the PCA. In FIG. 7, graph (a) corresponds to the MLP model, and graph (b) corresponds to the MedTextSeg method/model of the present disclosure. In the graphs, each symbol corresponds to a sentence in the test set, and its shape (i.e., triangle, circle, square etc.) denotes its ground truth section classification. For a hypothetical model providing ideal performance in correctly assigning section classifications to sentences, sentences with the same section classification would be clustered together and sentences belonging to different sections would exist in different, geometrically distant, clusters.

For the purposes of illustration, ovals have been drawn to indicate certain groupings of the symbols that are apparent from inspecting the graphs. Referring to FIG. 7(a), oval 702 contains only circles associated with the classification label 'procedure', oval 704 contains only triangles associated with the classification label 'side info', but oval 708 contains a mixture of all of the classification labels. Referring to FIG. 7(b), oval 710 contains almost exclusively circles associated with the classification label 'procedure', oval 712 contains only triangles associated with the classification label 'side info', and oval 714 contains only plus symbols associated with the classification label 'reason for exam'. From FIG. 7, it is apparent that the section separability in the sentence representations induced by the model of the present disclosure MedTextSeg as in FIG. 7(b) is more pronounced than for MLP as in FIG. 7(a). This qualitative analysis aligns with the empirical analysis, that the third sentence representations $u_i$ of the present disclosure are able to better capture section semantics and their overall topicality.

Figure 8:
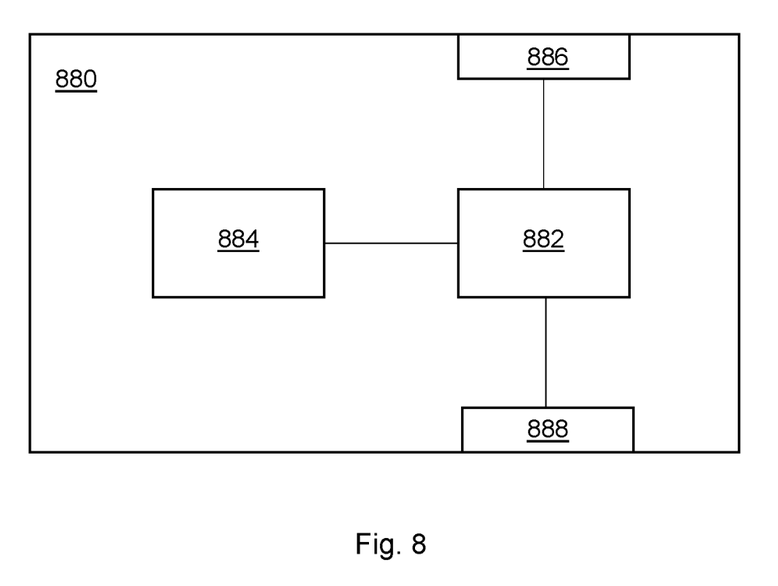
FIG. 8 is a diagram illustrating schematically an apparatus according to an example.

Referring to FIG. 8, there is illustrated an exemplary apparatus 880. The apparatus 880 comprises an input interface 886, an output interface 888, a processor 882, and a memory device 884. The processor 882 and the memory device 884 may be configured to perform the method according to any one of the examples described above with reference to FIGS. 1 to 7. The memory device 884 may store computer readable program code which, when executed by the processor 882 case the processor 882 to perform the method according to any one of the examples described above with reference to FIGS. 1 to 7. The computer readable program code may be stored on any computer readable medium, for example, one or more non-transitory computer readable media.

For example, the input interface 886 may receive a medical text report (or text thereof, or segmented sentences thereof, or word embeddings of a plurality of words of each of the sentences thereof), the processor 882 may implement the method described above with reference to FIG. 1 to the medical text report (or the data thereof), and the processor 882 may output, via the output interface 888, data representing the section classification assigned to each sentence, for example the output data as described above with reference to FIG. 3 or 4. In some examples, the output data may be transmitted to an structured storage (not shown) so that the output data is stored in the structured storage, for example as described above with reference to FIG. 3. In some examples, the output data may be transmitted to a display device (not shown) to allow a user to review the output data, for example as described above with reference to FIG. 4. In some examples, the output data may be stored, alternatively or additionally, in the memory device 884.

As another example, alternatively or additionally, the input interface 886 may receive a training data set as per any one of the examples described above, the processor 882 may implement training of a neural network for example as described above with reference to FIG. 6, and the processor 882 may output, via the output interface 888, the trained neural network or data representing the trained neural network. In some examples, the trained neural network or data representing the trained neural network may be stored in an external storage (not shown) or transmitted to another computer (not shown) for use by the other computer (not shown) to perform the method according to any one of the examples described above with reference to FIGS. 1 to 5. In some examples, the trained neural network or data representing the trained neural network may be alternatively or additionally stored in the memory device 884 or another local storage of the apparatus 880, for example for use by the apparatus 880 in implementing the method according to any one of the examples described above with reference to FIGS. 1 to 5.

The apparatus 880 may be implemented as a processing system and/or a computer. It will be appreciated that the methods according to any one of the examples described above with reference to FIGS. 1 to 7 are computer implemented methods, and that these methods may be implemented by the apparatus 880.

The above examples are to be understood as illustrative examples of the invention. It is to be understood that any feature described in relation to any one example may be used alone, or in combination with other features described, and may also be used in combination with one or more features of any other of the examples, or any combination of any other of the examples. Furthermore, equivalents and modifications not described above may also be employed without departing from the scope of the invention, which is defined in the accompanying claims.

What is claimed is:

1. A computer implemented method for segmenting a medical text report into sections, the method comprising:
   (a) for at least one sentence of the medical text report, obtaining word embeddings of a plurality of words of the sentence;
   (b) determining a first sentence representation for the sentence by:
     inputting the word embeddings of the plurality of words of the sentence sequentially into a first neural network to generate a word-level context representation for the sentence; and
     inputting the word-level context representation for each sentence sequentially into a second neural network to generate the first sentence representation for each sentence;
   (c) determining a second sentence representation for the sentence by:
     applying an aggregating operation to the word embeddings for the sentence to generate an aggregated representation for the sentence; and
     inputting the aggregated representation for each sentence sequentially into a third neural network to generate the second sentence representation for each sentence;
   (d) determining a third sentence representation based on a combination of the first sentence representation and the second sentence representation for the sentence;
   (e) determining a section classification for the sentence by inputting the third sentence representation for the sentence into a section classifier; and
   (f) assigning the sentence the section classification determined for the sentence.

2. The computer implemented method according to claim 1, wherein the method further comprises:
   (g) generating output data in which text of the medical text report is segmented into sections, each section being associated with a particular section classification and including those sentences of the medical text report to which the particular section classification has been assigned.

3. The computer implemented method according to claim 2, wherein the method further comprises:
   (h) storing the output data in a structured storage such that each section is stored in association with a respective associated section classification.

4. The computer implemented method according to claim 1, wherein generating the word-level context representation for each sentence comprises, for each word of the sentence:
   determining a score indicating a relevance of the word to a context of the sentence; and weighting a contribution associated with the word to the word-level context representation using the score determined for the word.

5. The computer implemented method according to claim 4, wherein, for each word of the sentence, the contribution associated with the word to the word-level context representation comprises a hidden state, associated with the word, of a recurrent unit of the first neural network.

6. The computer implemented method according to claim 5, wherein the context of the sentence is represented by an aggregation of hidden states associated with all of the words of the sentence.

7. The computer implemented method according to claim 1, wherein the third sentence representation is determined based on a concatenation of the first sentence representation and the second sentence representation.

8. The computer implemented method according to claim 1, wherein applying the aggregating operation comprises taking a mean of the word embeddings of the plurality of words of the sentence.

9. The computer implemented method according to claim 1, wherein one or more of the first neural network, the second neural network and the third neural network comprise a bidirectional Recurrent Neural Network.

10. The computer implemented method according to claim 1, wherein one or more of the first neural network, the second neural network and the third neural network comprise one or more Gated Recurrent Units.

11. The computer implemented method according to claim 1, further comprising:
   providing training data, the training data comprising a plurality of medical text reports, each medical text report comprising a plurality of sentences, the training data further comprising a ground truth section classification for each sentence indicating a particular section of the medical text report to which the sentence belongs; and
   training the first neural network, the second neural network, the third neural network and the section classifier based on the training data so as to minimize a loss function between the section classifications determined for the sentences by the section classifier and corresponding ground truth section classifications for the sentences.

12. A computer-implemented method of training a neural network for segmenting a medical text report into sections, the medical text report comprising a plurality of sentences, the method comprising:
   providing the neural network, the neural network including
     (a) a first sentence representation module comprising:
       a first neural network configured to generate, for each sentence, a word-level context representation for the sentence based on sequential input of word embeddings of a plurality of words of the sentence;
       a second neural network configured to generate, for each sentence, a first sentence representation for the sentence based on sequential input of the word-level context representation for the sentence, (b) a second sentence representation module comprising:
  a third neural network configured to generate, for each sentence, a second sentence representation based on sequential input of an aggregated representation for the sentence, the aggregated representation having been generated by applying an aggregating operation to the word embeddings of the plurality of words of the sentence, and
(c) a section classifier configured to, for each sentence, determine a section classification for the sentence based on input of a third sentence representation for the sentence, the third sentence representation being a combination of the generated first sentence representation and the generated second sentence representation for the sentence;
providing training data, the training data comprising a plurality of medical text reports, each medical text report comprising a plurality of sentences, the training data further comprising a ground truth section classification for each sentence indicating a particular section of the medical text report to which the sentence belongs; and
training the neural network based on the training data so as to minimize a loss function between the section classifications determined for the sentences by the section classifier and corresponding ground truth section classifications for the sentences.

13. The computer-implemented method according to claim 12, wherein the loss function comprises a cross entropy between the section classifications determined for the sentences by the section classifier and the corresponding ground truth section classifications for the sentences.

14. The computer-implemented method according to claim 12, wherein one or more of the first neural network, the second neural network and the third neural network comprise a bidirectional Recurrent Neural Network.

15. An apparatus, comprising:
a non-transitory memory device for storing computer readable program code; and
a processor in communication with the non-transitory memory device, the processor being operative with the computer readable program code to perform a method for segmenting a medical text report into sections, the medical text report comprising a plurality of sentences, the method comprising:
  (a) for each sentence, obtaining word embeddings of a plurality of words of the sentence;
  (b) for each sentence, determining a first sentence representation for the sentence by:
    for each sentence, inputting the word embeddings of the plurality of words of the sentence sequentially into a first neural network to generate a word-level context representation for the sentence; and
    inputting the word-level context representation for each sentence sequentially into a second neural network to generate the first sentence representation for each sentence;
  (c) for each sentence, determining a second sentence representation for the sentence by:
    for each sentence, applying an aggregating operation to the word embeddings for the sentence to generate an aggregated representation for the sentence; and
    inputting the aggregated representation for each sentence sequentially into a third neural network to generate the second sentence representation for each sentence;
  (d) for each sentence, determining a third sentence representation based on a combination of the first sentence representation and the second sentence representation for the sentence;
  (e) for each sentence, determining a section classification for the sentence by inputting the third sentence representation for the sentence into a section classifier; and
  (f) for each sentence, assigning the sentence the section classification determined for the sentence.

16. The apparatus according to claim 15, wherein generating the word-level context representation for each sentence comprises, for each word of the sentence:
determining a score indicating a relevance of the word to a context of the sentence; and weighting a contribution associated with the word to the word-level context representation using the score determined for the word.

17. The apparatus according to claim 16, wherein, for each word of the sentence, the contribution associated with the word to the word-level context representation comprises a hidden state, associated with the word, of a recurrent unit of the first neural network.

18. The apparatus according to claim 17, wherein the context of the sentence is represented by an aggregation of hidden states associated with all of the words of the sentence.

19. The apparatus according to claim 15, wherein the third sentence representation is determined based on a concatenation of the first sentence representation and the second sentence representation.

20. The apparatus according to claim 15, wherein applying the aggregating operation comprises taking a mean of the word embeddings of the plurality of words of the sentence.

* * * * *